United States Patent [19]
Dan et al.

[11] Patent Number: 5,968,830
[45] Date of Patent: Oct. 19, 1999

[54] SOYBEAN TRANSFORMATION AND REGENERATION METHODS

[75] Inventors: Yinghui Dan; Nancy A. Reichert, both of Mississippi State, Miss.

[73] Assignee: Mississippi State University, Mississippi State, Miss.

[21] Appl. No.: 08/825,469

[22] Filed: Mar. 28, 1997

[51] Int. Cl.$^6$ .............................. C12N 5/10; C12N 15/82; A01H 5/00

[52] U.S. Cl. .......................... 435/469; 435/419; 435/426; 435/430; 800/312

[58] Field of Search ................................ 435/172–3, 419, 435/426, 430; 800/DIG. 26

[56] References Cited

U.S. PATENT DOCUMENTS 5,416,011  5/1995  Hinchee et al. ...................... 435/172.3

OTHER PUBLICATIONS

Liu et al. Somatic embryogenesis in soybean via somatic embryo cycling. In Vitro Cell. Dev. Biol. 28P:153–160, Jul. 1992.

Sharma et al. High frequency plant regeneration in tissue cultures of *Glycine clandestina*—a wild relative of soybean. Phytomorphology. 43(1&2):29–33, Jan.–Jul. 1993.

Liu et al. Somatic embryo cycling: evaluation of a novel transformation and assay system for seed–specific gene expression in soybean. Plant Cell, Tissue and Organ Culture. 47:33–42, Mar. 1996.

Yuqing et al. Rapid and efficient regeneration from cotyledonary explants of soybean cultivars (*Glycine max* L.). J. Genet. & Breed. 49:339–342, 1995.

Brown, D.C.W., and T.A. Thorpe. 1986. Plant regeneration by organogenesis, pp. 49–65. In: Vasil, I.K. (Ed.) Cell Culture and Somatic Cell Genetics, vol. 3, Academic Press, Inc., Orlando, FL.

Dan, Y., and N.A. Reichert. 1988. Organogenic regeneration of soybean from hypocotyl explants. In Vitro Cell. Dev. Biol. 34P:14–21.

Dodds, J.H., and L.W. Roberts. 1995. Somatic embryogenesis, pp. 101–113. In: Experiments in Plant Tissue Culture, 3rd Ed., Cambridge University Press, New York, NY.

Gray, D.J. 1996. Nonzygotic embryogenesis, pp. 133–147. In: Trigiano, R.N., and D.J. Gray (Eds.) Plant Tissue Culture Concepts and Laboratory Exercises, CRC Press, Inc., Boca Raton, FL.

Kameya, T., and J. Widholm. 1981. Plant regeneration from hypocotyl sections of Glycine species. Plant Sci. Lett. 21:289–294.

Liu, K.S. 1997. Agronomic characteristics, production, and marketing, pp. 1–24. In: Soybeans: Chemistry, Technology, and Utilization, Chapman and Hall, New York, NY.

Pierik, R.L.M. 1987. Vegetative propagation, pp. 183–230. In: In Vitro Culture of Higher Plants, Martinus Nijhoff Publishers, Dordrecht, The Netherlands.

Poehlman, J.M. 1987. Breeding Soybeans, pp. 421–450. In: Breeding Field Crops, Van Nostrand Reinhold, New York, NY.

Sengupta–Gopalan, C., N.A. Reichert, R.F. Barker, T.C. Hall, and J.D. Kemp. 1985. Developmentally regulated expression of the bean β–phaseolin gene in tobacco seed. Proc. Natl. Acad. Sci. USA 82:3320–3324.

Schwarz, O.J., and R.M. Beaty. 1996. Propagation from nonmeristematic tissues—organogenesis, pp. 95–104. In: Trigiano, R.N., and D.J. Gray (Eds.) Plant Tissue Culture Concepts and Laboratory Exercises, CRC Press, Inc., Boca Raton, FL.

Widholm, J.M., S. Rick. 1983. Shoot regeneration from *Glycine canescens* tissue cultures. Plant Cell Rep. 2:19–20.

*Primary Examiner*—Douglas W. Robinson
*Assistant Examiner*—Thanda Wai
*Attorney, Agent, or Firm*—Oblon, Spivak, McClelland, Maier & Neustadt, P.C.

[57] ABSTRACT

A method of transforming and regenerating soybean plants relies on selection of hypocotyl explants as the target material. Hypocotyl explants can be transformed either by microparticle bombardment with DNA-coated microparticles of inert metals, or by co-culturing with an Agrobacterium strain. The transformed explants can be successfully regenerated, using a protocol including culturing on a shoot induction medium, followed by transfer to a shoot elongation medium to form rooted plantlets, which are transplanted to soil.

11 Claims, No Drawings

SOYBEAN TRANSFORMATION AND REGENERATION METHODS

BACKGROUND OF THE INVENTION

1. Field of the Invention

This invention pertains to a method for transforming and regenerating soybeans. Specifically, a method of transforming and regenerating soybeans, using soybean hypocotyl explants, and either bacteria-mediated or biolistic methods (micro-particle bombardment) to effect genetic transformation of a large variety of cultivars, coupled with plant regeneration from the hypocotyls, provides a reliable means for introducing genetic variation.

2. Background of the Prior Art

Soybean [*Glycine max* (L.) Merr.] is one of the world's most important agronomic crops. Between 120 and 130 million acres are planted annually, resulting in 105 million tons of seed. Soybeans have dominated world oilseed production among the eight major oilseeds traded in international markets, accounting for over 97% of all world oilseed production since 1965. The value of the crop is estimated to be over 20 billion dollars. Both soybean oil and protein are used extensively in food products for human consumption. In the United States, 5% of the total protein is derived from grain legumes and up to 65% of the oil used by the food processing industry comes from soybean (Hoskin, USDA Econ. Res. 1–35 (1987), Smith and Huyser, 1–22 (1987).

A great deal of effort has been made towards the development of new cultivars of soybean with improved disease, pest, herbicide resistance along with increased nutritional value. However traditional breeding programs have been restricted because soybean germplasm is extremely narrow and the majority of the soybean cultivars in use are derived from very few parental lines Christou et al., TIBTECH 8:145–151 (1990).

The development of gene transformation techniques has created an alternate path to the genetic improvement of many crops such as increased disease, pest and herbicide resistance, as well as quality improvement. However, success with these approaches has been limited in soybean due to various in vitro difficulties attributed to soybean Christou, supra. The design of genetic engineering protocols for soybean would include the development of an efficient plant regeneration system.

The majority of reports on soybean regeneration utilized cotyledons from immature zygotic embryos induced to undergo somatic embryogenesis Liu et al., In Vitro Cell. Dev. Biol. 28P:153–160 (1992), which could entail protracted culture periods. Soybean regeneration through short meristem cultures resulted in up to 35% explants responding to plant regeneration 4 weeks after culture Kartha et al., Can. J. Bot., 59:1671–1679 (1981). Regeneration via organogenesis utilizing different explants has been reported with a maximum of 97% of explants responding and 3 shoots produced per explant 10 weeks after culture, and 38% of shoots developing roots for another 4 weeks Yeh et al., J. Argric. Assoc. China, 40:77–90 (1991). However, interactions between genotype and in vitro cultural conditions (medium, explant and light treatment) have not been reported in regeneration via organogenesis or meristem culture in soybean, although it has been studied in regeneration via somatic embryogenesis and was proven important Powell et al., Heredity 58:75–801 (1987); Komatsuda et al., Crop. Sci. 31:333–337 (1991).

U.S. Pat. No. 5,322,783, Tomes et al., is directed to a method for transformation of soybean tissue which calls for treating cotyledonary node cells with a cytokinin, and then bombarding the cells with microparticles carrying specific vectors and exgenogeous DNA. U.S. Pat. Nos. 5,169,770 and 5,376,543, Chee et al., focus on a different method of transforming soybeans, to produce transgenic plants. In the process described in these patents, seeds are germinated, and the meristematic or mesocotyl cell tissues are inoculated with bacterial cells, specifically Agrobacterium strains, which through infection, transfers DNA into these explants. Transgenic plants could ensue provided this transfection transformation was successful and occured prior to differentiation.

Any plant transformation program also requires a regeneration program. In U.S. Pat. No. 4,992,375, Wright et al., a process is described which calls for excising the cotyledonary node region from a donor plant, and culturing the explant in a nutrient media containing cytokinin, until shoots arose from resultant callus. The shoots are then rooted. U.S. Pat. No. 5,416,011, Hinchee et al., also utilizes a cotyledon explant, which requires removal of the hypocotyl, saving and separating the cotyledons and inserting a chimeric gene by inoculation with *Agrobacterium tumefaciens* vectors containing the desired gene. This reference, and many others, employ the GUS histochemical marker to determine successful transformation.

Generally, the processes developed are categorized by a variety of inadequacies. Reliable transformation and regeneration is not accomplished. The formation of shoots, and eventual rooting, takes place only in a tiny fraction of the cases. Further, successful transformation and successful regeneration are frequently cultivar-specific, with no broad success. Among investigators reporting random, and overall poor success, are Wayne et al., Plant Mol. Biol. (1988); Finer et al., In Vitro Cell. Dev. Biol. (1991); Sato et al., Plant Cell Reports (1993); Moore et al., Plant Cells Reports (1994); Parrott et al., In Vitro Cell. Dev. Biol. (1994) and Stewart et al., Plant Physiol. (1996). While limited successes in producing transgenic plants are reported (e.g., 1 out of 195 in Parrott et al. 1994), success is random, and not predictable.

Accordingly, it remains an object of those of skill in the art to develop a reliable, repeatable and non-cultivar-limited method for transforming and regenerating soybeans.

SUMMARY OF THE INVENTION

The above objects, and other objects set forth in more detail in the disclosure following, are achieved by employing a soybean regeneration protocol, which can be coupled with transformation protocols employing either biolistic processes or bacterial transfection, uses hypocotyl explants to obtain adventitious regeneration across all tested cultivars. While differences in response are observed within cultivars, all cultivars give a very positive response. The hypocotyl explant is cut from a seedling, just below the cotyledonary attachments, and then either split longitudenly into two pieces, or left intact. Split hypocotyl explants are placed split side down on a shoot induction media, while intact explants are placed upright on the shoot induction media, with the basipetal end submerged in the media. The explant is incubated for four weeks at about 25° C. under either continuous darkness, or a 16 hr photoperiod. Various genotypes respond better to darkness or the photoperiod regime.

Either the acropetal end of the hypocotyl section, or individual shoots, are excised and placed on a shoot elongation medium, and cultured on the medium for another 2–4 weeks under a 16 hr photoperiod. When the shoots exceed about 5 mm, they are placed on a rooting medium for a period of 1–2 weeks, and then the rooted plantlets are transferred into a conventional soilless potting medium, then acclimatized. Conditions of about 25° C. and a 16 hr photoperiod are maintained.

This regeneration program can be used to regenerate existing cultivar stocks. In a preferred embodiment, transformant candidates are selected, and regenerated through this process. The hypocotyl explant is also ideal for transformation.

One transformation protocol calls for microparticle bombardment, a biolistic process. In this process, the hypocotyl explants are cultured as above, by being placed upright on a shoot induction medium. The explants are clustered in the target area, and maintained on the medium one day prior to bombardment under continuous darkness.

Transforming microparticles are prepared by suspending the micro projectile, preferably of gold or other inert metals such as tungsten in a solution of the desired chimeric DNA, followed by mixing and centrifuging. The supernatant is removed, leaving the DNA-coated microparticle. The hypocotyl explants are bombarded using commercially available DNA delivery systems. Within a week following bombardment, the explants are transferred onto a medium for selective growth of transformed tissues, and grown under continuous darkness, then transferred onto a shoot elongation medium. On the shoot elongation medium, a 16 hr photoperiod is employed, as set forth above in connection with the regeneration protocol. In general, control or non-transformed hypocotyl tissues die within 30–40 days after placement on the media containing phosphinothricin or similar active agent. Surviving shoots are regenerated according to the above protocol.

In an alternative method, soybean transformation is effected via the *Agrobacterium tumefaciens* microorganism, or other Agrobacterium strains employed in previous attempts. The difference remains the use of the hypocotyl explant. Explant preparation is essentially the same as in the biolistic method. *A. tumefaciens* is pre-cultured to enhance its virulence. A preparation of the bacteria is placed on the acropetal end of each hypocotyl explant and co-incubated for 2–3 days under continuous darkness, or completely submerged in the bacterial solution for 30 min prior to co-incubation. Effective transfection/transformation may be enhanced by prior bombardment with uncoated gold micro projectiles, as described above. The co-incubated explants are then rinsed in an antibiotic, blotted dry, and returned to a shoot induction medium containing an antibiotic such as cefataxime (Claforan) at 500–700 mg/l in liquid or semi-solid shoot induction media with daily sub-cultures for approximately 4 days. The transformation protocol described above, following bombardment, is essentially followed thereafter, involving transfer to a medium for selective growth of transformed tissues in a 16 hr photoperiod. Again, a selection agent, such as phosphinothricin or geneticin (depending on resistance gene introduced) is employed. The media also contains Claforan. The regeneration protocol is followed, providing transgenic soybean plants.

DETAILED DESCRIPTION OF THE INVENTION

This invention includes methods of transforming soybean plants, as well as regeneration. Either the transformation or regeneration protocols can be used separately, but together, they provide an effective method for obtaining transgenic soybean plants, to answer the needs of commercial farming and manufacturing. Accordingly, while both the regeneration protocol, and each transformation protocol, are described separately, it should be understood that they can, and preferably are, used in combination.

The invention is disclosed below, in terms of generic description and by specific example. The success of the inventive techniques described below, however, lie in the identification of hypocotyl explants, and suitable culture conditions, ignored or discarded in the prior art, as the "germ material" for treatment.

Express descriptions of both the regeneration method and results, from specific examples, and the transformation methods, together with results from specific examples, are set forth below, to aid in understanding of the invention. Preceding those is a "step-by-step" summary of first the regeneration process, and then the two transformation processes, to aid the reader in understanding the examples reported. It should be understood that the processes described herein are particularly advantageous in that they employ conventional materials, including available media, gene gun and transformation vectors. Accordingly, substitutes for these, established in the art, can be equally employed. Moreover, specific times, amounts and the like are intended for example only, and are not restrictive.

Protocol for Soybean Regeneration from Hypocotyl Explants

1. Materials

Thirteen public soybean lines adapted for growth in Mississippi: Centennial, Crawford, Epps, Essex, Hartwig, Hill, Lamar, Lyon, Manokin, PI 398469, Sharkey, Vernal, and York were utilized. Other lines are available and can be used.

2. Germination

Mature soybean seeds are rinsed in 70% ethanol for 1 min and surface-disinfested for 20 min in a 20% (v/v) bleach solution with continuous shaking at 210 rpm, then rinsed four times with sterile distilled water. Sterile seeds are germinated in Magenta™ boxes containing eight layers of cheesecloth and 45 ml of liquid SI2 medium [composed of MS basal salts (Murashige and Skoog, 1962), B5 vitamins (Gamborg et al., 1968), 5 $\mu$M 6-benzyladenine (BA), 3% (w/v) sucrose, pH 5.8] at room temperature under continuous darkness. Hypocotyl explants are excised from seedlings approximately seven days after germination.

3. Explant

Hypocotyl explant: One section approximately 5 mm in length is cut from each seedling just below the cotyledonary attachments, then split longitudinally into two pieces or left intact. Those left intact will be placed upright on shoot induction media (basipetal end submerged in media) or placed split-side down on shoot induction media.

4. Shoot Induction

Hypocotyl explants are placed on SI2 medium (above) containing 0.8% (w/v) phytagar or SI1 medium (same as SI2 except twice the amount of BA—10 $\mu$M) and incubated for four weeks at 25° C. under continuous darkness or a 16 hr photoperiod (approx. 75 $\mu$E-m$^{-2}$s$^{-1}$), depending on the genotype.

5. Shoot Elongation

The responding part (acropetal end) of the hypocotyl section or individual shoots are excised and placed on a shoot elongation medium (SE7) composed of B5 basal salts and vitamins (Gamborg et al., 1968), 0.36 $\mu$M BA, 3% (w/v) sucrose, 0.8% (w/v) phytagar, pH 5.8. They are cultured on this medium for 2–4 weeks at 25° C. under a 16 hr photoperiod (approx. 75 $\mu$E-m$^{-2}$s$^{-1}$).

6. Plant Regeneration

Shoots longer than 5 mm are placed on rooting medium R2 [MS basal salts (Murashige and Skoog, 1962), B5 vitamins (Gamborg et al., 1968), 12.5 $\mu$M indole-3-butyric acid (IBA), 3% (w/v) sucrose, 0.8% (w/v) phytagar, pH 5.8] or medium R4 (same as R2 except it contains 29.2 $\mu$M IBA), depending on genotype for 1–2 weeks, and rooted plantlets were transferred onto G medium (same medium as in 5., except it does not contain BA) for 1–3 additional weeks, prior to transplanting to soil. Cultures were maintained at 25° C. under a 16 hr photoperiod (approx. 75 $\mu$E-m$^{-2}$s$^{-1}$).

Protocol for Soybean Transformation via Particle Bombardment

1. Explant Preparation

Pre-culture hypocotyl explants after placing them upright on shoot induction medium SI2 (basipetal end submerged in medium) next to one another within a 2.5 cm diameter for one day under continuous darkness as described in the regeneration protocol. Approximately 25–30 hypocotyl explants can be placed in the designated 2.5 cm diameter target area.

2. Coating Microprojectiles with DNA

Suspend prepared microprojectiles (gold, 1.0 $\mu$m diameter, 1350 $\mu$g) in 25 $\mu$l (30 $\mu$g) of DNA in solution, add 220 $\mu$l sterile water, 250 $\mu$l 2.5 M $CaCl_2$ and 50 $\mu$l 0.1 M spermidine. Mix thoroughly and vortex for 10 min. Centrifuge for 1 min and remove supernatant. Resuspend pellet and place mixture on microprojectiles for delivery of 10 $\mu$g DNA and 450 $\mu$g gold per shot.

3. Bombardment of Hypocotyl Explants

Clean all gun parts thoroughly with 70% ethanol. Hypocotyl explants are bombarded twice using the Biolistic Particle Delivery System (PDS-1000/He; Bio-Rad). The plasmid pAHC25 containing UBI-GUS and UBI-Bar genes Christensen et al., Transgenic Res. 5:213–218 (1996) is utilized or other desired expression system may be employed. The dish containing hypocotyl explants is placed 96 mm below the rupture disk, with a gap distance of approximately 1.0 cm and a helium pressure of 1350 psi. Bombarded tissues are cultured under continuous darkness as per the regeneration protocol.

4. Screening and Selecting Transformed Tissues

Three to seven days after bombardment, hypocotyl explants are transferred onto medium SI2-5P (medium SI2+5.0 mg/l phosphinothricin) for selective growth of transformed tissues and grown for three weeks under continuous darkness, then transferred onto shoot elongation medium SE7-5P (medium SE7+5.0 mg/l phosphinothricin) and transferred to a 16 hr photoperiod as per the regeneration protocol. In general, control (bombard without exogenous DNA) hypocotyl tissues die within 30–40 days after placement on media containing a 5.0 mg/l phosphinothricin.

5. Regenerating Transgenic Plants

Regenerated shoots that survive the above selection will be placed on media described in steps 5 and 6 of the regeneration protocol, with or without the presence of phosphinothricin.

Protocol for Soybean Transformation via Bacterial Transfection/Transformation

For soybean transformation via *Agrobacterium tumefaciens*, steps 4 and 5 of the transformation protocol described on the previous page will essentially remain the same. New Steps:

1. Intact hypocotyl explants are pre-cultured by placing them on a shoot induction medium for one day under continuous darkness.

2. *A. tumefaciens* are pre-cultured with acetosyringone or tobacco leaf extracts to enhance its virulence response. One drop of the bacteria preparation is placed on the acropetal end (upper surface) of each soybean hypocotyl explant and co-incubated for 2–3 days under continuous darkness. [Additional wounding prior to addition of *A. tumefaciens* may be achieved by bombardment with gold microprojectiles or other inert metal such as tungsten (without DNA)].

3. Hypocotyl explants are rinsed in a 1000 mg/l solution of Claforan, blotted dry, then placed back on the shoot induction medium. One week later, step 4 of the transformation protocol is followed, except the media also contains Claforan at 500 mg/l and geneticin at 40 mg/l. Subsequent media in step 5 of the transformation protocol may be amended to contain Claforan plus geneticin at the above concentrations. Culture conditions, as described in the regeneration protocol, are followed.

SPECIFIC EXAMPLES

Soybean Regeneration

Materials and Methods

Thirteen public soybean lines (12 cultivars and one plant introduction) adapted to Mississippi were utilized in development of adventitious organogenic regeneration protocols. They included: Centennial, Crawford, Epps, Essex, Hartwig, Hill, Lamar, Lyon, Manokin, PI 398469, Sharkey, Vernal, and York. Mature soybean seeds were rinsed in 70% ethanol one min, surface-disinfested in a 20% bleach solution (5.25% sodium hypochlorite) for 20 min with continuous shaking at 210 rpm, then rinsed four times with sterile distilled water. Seeds were germinated in Magenta™ boxes on eight layers of cheesecloth soaked with 45 ml liquid SI1 medium containing 5 $\mu$M BA in basal MS medium [MS basal salts (17), B5 vitamins (10), 3% (w/v) sucrose, pH 5.8] at room temperature in continuous darkness. For all experiments, hypocotyl explants were excised from seedlings seven days after imbibition (culture initiation).

One hypocotyl section, 5 mm in length, was cut from each seedling, with placement of the acropetal cut just below the cotyledonary attachments. Each hypocotyl section was split longitudinally into two and each placed cut-side down onto one of three semi-solid (0.8% w/v phytagar) media (SI1, SI2, SI3). Medium SI2 was identical to that listed above, and the other two differed only in regard to plant growth regulator (PGR) amendments [SI1: 10 $\mu$M BA; SI3: 2.5 $\mu$M BA+1 $\mu$M 1-naphthaleneacetic acid (NAA)]. Each petri plate (100×25 mm) contained six split hypocotyl explants. Plates were incubated at 25° C. under continuous darkness or under a 16 hr photoperiod (75 $\mu$E-m$^{-2}$s$^{-1}$; cool white fluorescent lights). Four weeks after culture initiation, explants were transferred onto fresh media (same as initial) and all placed under a 16 hour photoperiod for an additional four weeks.

Experiments were conducted as three factor experiments (13 genotypes×3 media×2 culture conditions) using a completely randomized design, with three replicate plates per treatment, and the experiment was repeated three times. Hypocotyl cultures were analyzed four weeks after experiment initiation for regeneration potential RP; percentage of explants capable of producing meristem-like structures or shoot primordia. After an additional four weeks, cultures were quantified for regenerative ability [RA; number of shoots produced per responding (RP-positive) explant] and regeneration efficiency (RE; number of shoots produced per explant plated). Data were analyzed using SAS PROC ANOVA and SAS PROC CORR with mean separations made with Duncan's multiple range test.

After four weeks on SI2 medium, responding acropetal ends from 'Epps' and 'Lyon' were excised (1.0–2.0 mm length cross-section) and placed onto various shoot elongation media (SE1–SE9; Table 1). Those two cultivars were chosen due to consistently high responses in shoot organogenesis. Eight to 33 shoots (reps) were placed onto each medium and cultured at 25° C. under a 16 hr photoperiod for four weeks. Shoots greater than five mm in length were placed onto one of four rooting media: MS-based R1 [4.2 $\mu$M indole-3-butyric acid (IBA)], R2 (12.5 $\mu$M IBA), R3 (20.8 $\mu$M IBA) and R4 (29.2 $\mu$M IBA). Shoots were incubated at 25° C. under a 16 hr photoperiod.

To determine if cultures could retain adventitious shoot production over time, eight week old hypocotyl cultures of cultivars Centennial, Hill, Lyon and Vernal were utilized. Areas producing shoots were excised at 25° C. under a 16 hr photoperiod. Every month, for a total of 12 months, shoot-producing areas were excised and placed onto fresh media for subsequent culture.

Results

Adventitious Shoot Organogenesis

Hypocotyl tissues from all cultivars swelled two to three days after culture initiation, regardless of medium or culture condition. The acropetal end began to develop meristem-like structures or shoot primordia after four to 19 days in culture and was dependent on cultivar, medium and culture conditions. On some explants, callus would arise from the explant and became visible from six to 15 days after culture initiation. However, meristem-like structures and shoot primordia usually arose without intervening callus although amorphous callus developed later around the hypocotyl explants. In most cases, meristem-like structures, shoot primordia and shoots developed solely on the acropetal end of the soybean hypocotyl explant as had been observed in *G. canescens*. For all genotypes, adventitious shoots were clearly visible emerging from the acropetal end eight weeks after culture initiation. One noted exception was in 'Crawford', where occasionally adventitious shoots formed along the non-cut areas (stem epidermis). Only one hypocotyl explant (closest to cotyledons) was taken from each germinated seedling so the contribution of explant location could not be studied. However, hypocotyl sections located closest to the cotyledons were most responsive for numbers of adventitious shoots generated in *G. canescens*, Kameya and Widholm Plant Sci. Lett. 21:289–294 (1981).

Genotype Effects

Although genotype-independence was confirmed by the successful production of adventitious shoots on hypocotyl explants from all genotypes, relative individual responses varied (Table 2). Cultivars Epps and Lyon demonstrated significantly higher regeneration potentials than Crawford, Sharkey and York. However, the eight other genotypes responded as well as the best two cultivars with 60–75% of the explants responding (Table 2). In comparison, cultivars Corsoy and Dunn gave explant responses which ranged from 3–10%, Kimball et al., Crop. Sci. 13:758–760 (1973). Four cultivars responded as well as Lyon for regenerative ability with 5.1–7.1 shoots generated per responding explant, but only two performed as well as Lyon in regeneration efficiency yielding 3.8–5.0 shoots per hypocotyl explant plated (Table 2). Cultivars Centennial, Epps and Lyon consistently gave the greatest responses in all three categories. In regeneration via somatic embryogenesis, genotype-dependence was noted, Bailey et al., Plant Sci. 93:117–120 (1993) however, it was not determined as important in regeneration via organogenesis Barwale et al., Planta 167:473–481 (1986). Development of our genotype-independent organogenic regeneration protocol further supported that observation.

Medium and Culture Effects

Among all genotypes tested, media SI1 and SI2 yielded significantly greater numbers for both regeneration potential and efficiency than medium SI3 (Table 3). Overall, medium SI2 appeared to be the best medium by yielding the greatest responses for both parameters. Within each cultivar, culture conditions (16 hr photoperiod vs. darkness) did not affect any parameter tested, except in 'York' where initial darkness significantly enhanced regenerative ability (8.4 vs. 4.9 shoots produced per responding explant). Interactions between medium and culture condition also did not affect outcomes, except in 'Hill' where the interaction of medium SI2 and the 16 hr photoperiod yielded 10.1 shoots per responding explant versus 1.7 when cultured under continuous darkness.

Under the ideal combinations of medium and culture condition, regeneration potential for the 13 genotypes ranged from 72–95%, regenerative ability yielded 3.5–15.4 shoots per responding explant and 3.3–9.2 shoots per explant plated (regeneration efficiency). The three best genotypes (cultivars Centennial, Epps, Lyon) responded at 83–95%, and yielded 8.4–11.5 shoots per responding explant and 8.1–9.2 shoots per explant plated.

Of the cultivars tested (Centennial, Epps, Lyon), adventitious shoots also emerged from the acropetal end of intact hypocotyl explants (not split longitudinally) when cultured upright (basipetal end submerged into appropriate media), and their regeneration potential (92%, 100%, 100%, respectively) and regeneration ability (12.4, 14.9, 19.6, respectively) were greater than those of split hypocotyl explants. These explants make ideal targets for biolistics-based and *Agrobacterium tumefaciens*-based transformation protocols and we have demonstrated their efficacy in transient gene and stable expression assays, below.

Correlations Among Measured Parameters for Shoot Initiation

Correlation analysis determined that shoot regeneration potential was independent of both regenerative ability and regeneration efficiency. This was expected, since the percentages of explants capable of responding should not be an indicator of how many shoots are ultimately produced per explant. It was determined that regenerative ability and regeneration efficiency were correlated (R=0.88, P<0.01), which is understandable since one (RA) is essentially a subset of the other (RE). Other researches had attempted to correlate various measured parameters with regeneration success. Barwale et al., Theor. Appl. Genet. 72:423–428 (1986) determined that numbers of shoots capable of forming at the cotyledonary node could not be correlated with a genotype's ability to regenerate via somatic embryogenesis or organogenesis.

Shoot Elongation and Rooting

After four weeks on SI2 in continuous darkness, responding acropetal ends of 'Epps' and 'Lyon' were excised and placed on various shoot elongation media (Table 1) for four weeks. For 'Epps', media SE1–SE3 gave optimal responses for numbers of elongated shoots per explant (Table 4). Medium SE3 also yielded a greater percentage of shoots longer than 0.5 cm. In comparison, 'Lyon' performed better on medium SE2. It was determined that glutamine did not consistently aid in shoot elongation, although it had been reported to enhance adventitious shoot regeneration in primary soybean leaf tissues Wright et al., Plant Cell. Rpt. 6:83–89 (1987). It appeared that BA at 0.36 $\mu$M was an important media additive in regard to yielding the greatest numbers of shoots capable of elongation and an increased percentage that were longer than 0.5 cm.

Since medium SE2 did not allow shoots to continue to elongate or produce additional shoots for further subculture one month after culturing on SE2, new media formulations were tested. 'Lyon' was utilized in screenings, since it was chosen for development of biolistics-based and *Agrobacterium tumefaciens*-based transformation protocols. Of the remaining five media tested (SE5–SE9; Table 1), medium SE7 significantly enhanced shoot elongation yielding greater numbers of shoots at least 0.1 cm in length and higher percentages of shoots longer than 0.5 cm (Table 4). It appeared that Gamborg's B5 basal salts Gamborg et al., Exp. Cell. Res. 50–151–158 (1968) was successful. Media containing other additives (IBA, MES, and $GA_3$) contributed to results consistent with SE2, but were not as good as SE7 (Table 4). Acropetal ends from 'Centennial' and 'Epps' were placed on SE7 and they generated 11.2 and 13.4 shoots per explant, respectively. Medium SE7 was also used to maintain and subculture excised shoots after separation from hypocotyl explants.

For the cultivars tested (Centennial, Epps, Lyon), excised shoots produced roots within two weeks after being placed on rooting medium R1 or R2. Frequencies of rooting were 85% (R1) and 100% (R2) for 'Centennial', 80% for 'Epps' (R1 and R2), with 40% (R1) and 55% (R2) for 'Lyon'. Two additional rooting media were compared for 'Lyon' which yielded rooted shoots at frequencies of 73% (R3) and 87% (R4) within two weeks. It has been noted previously that a maximum of 40–60% of soybean adventitious shoots developed roots Mante et al., In Vitro Cell. Dev. Biol. 25P:385–388 (1989). After 1–2 weeks on rooting media, plantlets were transferred onto MS-based, Murashige et al., Physiol. Plant. 15:473–497 (1962) medium plus 5 mM glutamine or B5-based medium (Gamborg et al., 1968) without PGRs for 1–3 weeks for further plant development prior to transplanting into soil. Plantlets stunted and died when they were maintained on initial rooting media or when transferred onto MS medium without glutamine after roots appeared.

With our protocol, intact regenerated plantlets cold be obtained within 13 weeks (shoot induction under darkness for 4 weeks, shoot elongation under a 16 hr photoperiod for 4 weeks, rooting and plantlet elongation for 3–5 weeks). To date, 90% of the plantlets transplanted to soil survived. 'Lyon' transplants have been grown to maturity and overall morphology and growth were similar to the original cultivar.

Discussion

Our unique genotype-independent adventitious regeneration protocol could also be utilized to produce plants from all 13 lines tested. The organogenic capacity could be maintained for at least one year, as demonstrated in cultivars Centennial, Vernal, Hill and Lyon. In our study, 5 $\mu$M BA induced adventitious shoot organogenesis on hypocotyl explants, the same concentration reported successful with cotyledon and cotyledonary node explants.

It is postulated that preconditioning hypocotyl explants by germinating soybean seeds in media containing 5 $\mu$M BA helped to induce the observed adventitious shooting response. Earlier research unsuccessful in generating shoots on hypocotyl explants from cultivars Bragg, Dunn, Essex and Wayne did not include a preconditioning step Kameya and Widholm (1981) supra, Widholm et al., Plant Cell Rpt. 2:19–20 (1983) and Wright, et al. (1987) supra. The described regeneration protocols have been successful on 13 soybean genotypes and have been demonstrated amenable to incorporation in biolistics-based and *Agrobacterium-tumefaciens*-based transformation protocols, discussed below.

TABLE 2

Effects of soybean genotype on regeneration potential (RP) regenerative ability (RA) and regeneration efficiency (RE) over all treatments.

| Genotype (Line) | Maturity Group | $RP^z$ | $RA^y$ | $RE^x$ |
| --- | --- | --- | --- | --- |
| Centennial | VI | 63 abc | 5.5 abc | 3.8 abc |
| Crawford | IV | 47 d | 1.4 f | 1.0 e |
| Epps | V | 75 a | 5.2 abc | 4.0 abc |
| Essex | V | 63 abc | 2.5 def | 1.9 de |
| Hartwig | V | 65 abc | 2.7 def | 2.0 de |
| Hill | V | 60 abcd | 3.8 cde | 2.1 de |
| Lamar | VI | 67 ab | 3.3 cdef | 2.4 cde |
| Lyon | VI | 75 a | 7.1 a | 5.0 a |
| Manokin | IV | 63 abc | 1.9 ef | 1.5 e |
| PI 398469 | VI | 65 abc | 5.1 abc | 3.5 bcd |
| Sharkey | VI | 48 cd | 4.7 bcd | 2.1 de |
| Vernal | VI | 60 abcd | 2.8 def | 2.1 de |
| York | V | 52 bcd | 6.6 ab | 3.4 bcd |

Mean of 3 replicates (6 explants/rep) from each of three separate experiments. Means within a column not followed by the same letter differ significantly (Duncan's multiple range test, P < 0.05).
$^z$percentage of explants producing meristem-like structures or shoot primordia, determined after four weeks in culture
$^y$number of shoots produced per RP-positive explant, determined after eight weeks in culture
$^x$number of shoots produced per explant plated, determined after eight weeks in culture

TABLE 3

Effects of medium on regeneration potential (RP) and regeneration efficiency (RE) over all treatments.

| Medium | $RP^z$ | $RE^y$ |
| --- | --- | --- |
| SI1 | 70 a | 2.5 b |
| SI2 | 73 a | 4.3 a |
| SI3 | 42 b | 1.1 c |

Mean of 3 replicates (6 explants/rep) from each of three separate experiments. Means within a column not followed by the same letter differ significantly (Duncan's multiple range test, P < 0.05).
$^z$percentage of explant producing meristem-like structures or shoot primorida
$^y$number of shoots produced per explant plated

TABLE 1

Shoot elongation (SE) media formulations.

| Medium additive ($\mu$M) | Medium | | | | | | | | |
| --- | --- | --- | --- | --- | --- | --- | --- | --- | --- |
| | SE1 | SE2 | SE3 | SE4 | SE5 | SE6 | SE7 | SE8 | SE9 |
| BA | 0.89 | 0.36 | 0.36 | 0.36 | 0.36 | 0.36 | 0.36 | 0.36 | |
| $GA_3^z$ | | | | 0.15 | | 5.0 | | | |
| IBA | | | | | 0.03 | 0.03 | | | 3.3 |
| $MES^y$ | | | | | | | | | 3.0 |
| Glutamine (mM) | | | 5.0 | 5.0 | | | | | |

All media contained B5 vitamins (10), sucrose (30 g/l), phytagar (0.8%), pH 5.8. Media SE7 and SE9 were composed of B5 (10) basal salts, all others were composed of MS (17) basal salts (SE8 at half-strength).
$^z$gibbereliic acid
$^y$2-(N-morpholino)ethanesulfonic acid

TABLE 4

Shoot elongation on responding acropetal tissues four weeks after transfer.

| Medium | Cultivar | Percentage of shoots of length | | $RE^z$ |
|---|---|---|---|---|
| | | 0.1–0.5 cm | >0.5 cm | |
| | Epps | | | |
| SE1 | | 98 | 2 | 8.9 ± 1.4 |
| SE2 | | 97 | 3 | 11.2 ± 4.0 |
| SE3 | | 87 | 13 | 11.9 ± 2.9 |
| SE4 | | 100 | 0 | 4.3 ± 1.8 |
| | Lyon | | | |
| SE1 | | 100 | 0 | 3.3 ± 0.6 |
| SE2 | | 84 | 16 | 7.4 ± 3.3 |
| SE3 | | 100 | 0 | 2.7 ± 0.5 |
| SE4 | | 100 | 0 | 2.5 ± 0.4 |
| SE5 | | 89 | 11 | 7.3 ± 2.6 |
| SE6 | | 100 | 0 | 6.1 ± 1.9 |
| SE7 | | 80 | 20 | 17.3 ± 2.9 |
| SE8 | | 95 | 5 | 6.8 ± 2.0 |
| SE9 | | 85 | 15 | 5.0 ± 3.6 |

A 1.0–2.0 mm cross-section of tissue excised from responding hypocotyl sections (acropetal end) was placed on SE media. Each cross-section was considered a replicate with eight to 13 reps for 'Epps' and 10–33 reps for 'Lyon' per medium tested.
$^z$number of shoots per hypocotyl section at least 0.1 cm in length with standard deviation

Soybean Transformation

The soybean regeneration protocol described above is ideally used to regenerate transformed soybeans, after incorporation of exogenus DNA which provides desired characteristics not native to the soybean cultivars available. While soybean transformation is known in the art, prior art documentation of the same is discouraging. In Parrott et al., Plant Cell Rpt. 7:615–617 (1989), a process employing cotyledon tissues for co-cultivation with Agrobacterium strains to incorporate a zein gene was successful only in very low frequencies of less than 1%. Similarly, U.S. Pat. Nos. 5,169,770 and 5,376,543, Chee et al., describes transformation of soybean plants by Agrobacterium inoculation of meristematic or mesocotyl cells. These patents described the transformation of soybeans to express NPT II genes. This was achieved in employing the binary plasmid pGA482G. Additionally, a high sulphur storage protein gene, HSSP, and plasmid incorporating the same is set forth in these patents. A designed derivative is prepared, and attempts to transform soybeans are set forth. Yet, less than 1% of the plant tissues so treated are successfully transformed and regenerated.

Another attempt at soybean transformation is described in U.S. Pat. No. 5,416,011, Hinchee. This patent details the preparation of A. tumefaciens mediated transformation vectors. This patent also describes the use of a histochemical assay for GUS gene (β-glucuronidase) as a marker gene. The vectors and genes addressed in these patents can be employed in this invention.

To effectively transform soybeans, hypocotyl sections are taken, as described above, and infected with virulence-enhanced A. tumefaciens. Specifically, hypocotyl explants are prepared on SI2 medium for a day under continuous darkness. A. tumefaciens was pre-cultured and/or co-cultured with acetosyringone. In the alternative, tobacco leaf extracts, or other virulence enhancing agents could have been employed. One drop of the bacteria culture was placed on the acropetal end of each hypocotyl explant or the explants were immersed in the bacterial suspension for 30 min. The hypocotyl sections and bacteria are co-cultured on SI2 medium with acetosyringone for three days. The A. tumefaciens strain selected was pGV3850, containing a GUS gene controlled by CaMV 35S promoter and nos 3'; plus the neomycin phosphotransferase (NPT II) gene the construct of which was obtained from Clontech, Inc.

The treated hypocotyl explants were rinsed in an antibiotic solution (cefotaxime) and cultured in (solid or liquid) SI2 medium plus cefotaxime (500–700 mg/l) for four days with daily replacement of the medium. Explants were then assayed, both flourometrically and histochemically for transformed GUS activity.

Remaining sections were maintained on shoot initiation medium (SI2) plus antibiotic and a chemical (such as the antibiotic geneticin) to allow selective growth, thereafter following the rest of the regeneration protocol set forth above. The results of the flourometric and histochemical assays for each of the twelve cultivars tested are set forth in Tables 5 and 6.

In another alternative, hypocotyl explants are transformed via gene microparticle bombardment. As before, hypocotyl explants are placed on a shoot induction medium (SI1 or SI2) within a target cluster. In the transformation conducted, 25 explants were placed within the target area of 2.5 cm diameter. These explants, after one day in the medium, were bombarded (twice) with DNA-coated gold microprojectiles, 1.0 μm in diameter. Each bombardment delivered approximately 10 μg DNA (pAHC25) and 450 μg of gold. The particles were shot using 1,350 psi helium pressure.

The bombarded tissues were cultured in the dark for four weeks, and then subjected to a 16 hr photoperiod. Phosphinothricin was added to the SI media, to select for transformants. The GUS gene, introduced through pAHC25 was detected 2–3 days post-bombardment in all hypocotyl sections. Four weeks after bombardment, as many as 84% of the transformed, regenerated hypocotyls continued to express GUS, indicating numerous stable transformation events were obtained. GUS has been detected in developing adventitious shoots all throughout the shoots or in sectors and in surrounding hypocotyl tissues. These results are reflected in Table 7. Clearly, effective methods for transforming and regenerating soybean cultivars, using available technology and importantly selecting the hypocotyl section, are developed which are relatively genotype-insensitive, although variations between cultivars persist.

Applicants have disclosed this invention in terms of generic description, and specific example. Alternatives will occur to those of ordinary skill in the art without the exercise of inventive faculty. In particular, microparticle bombardment methods, and microparticle material selections, media compositions, periodisty and photoperiod length, etc. are all subject to modification. These modifications remain within the scope of the invention as disclosed, unless specifically excluded by limitations of the claims set forth below.

TABLE 5

GUS Activities in twelve cultivars when inoculating with Agrobacterium strains (with GUS gene and without GUS gene as control.)

| Cultivar | Total GUS activity ($\mu M$ MU/min/10 hypocotyls) when using Agrobacterium strain (with GUS gene) | Background GUS activity ($\mu M$ MU/min/10 hypocotyls) when using Agrobactertum strain (without GUS gene = background) | Net GUS activity ($\mu M$ MU/min/10 hypocotyls) when using Agrobacterium strain (with GUS gene |
|---|---|---|---|
| Vernal | 32.782 | 12.757 | 20.025 A[x] |
| Essex | 18.592 | 8.277 | 10.315 B |
| Centennial | 16.419 | 6.787 | 9.632 B |
| Lamar | 14.123 | 5.275 | 8.848 BC |
| Manokin | 17.539 | 10.707 | 6.832 BCD |
| Hartwig | 10.304 | 3.662 | 6.642 BCD |
| York | 13.574 | 7.246 | 6.328 BCD |
| Lyon | 11.581 | 5.488 | 6.093 BCD |
| Epps | 10.786 | 5.925 | 4.861 CD |
| Crawford | 10.181 | 5.588 | 4.593 CD |
| Sharkey | 7.370 | 4.883 | 2.487 D |
| PI 398469 | 10.035 | 7.594 | 2.441 D |

[x]Means within the column not followed by the same letter differ significantly (Duncan's multiple range test, $P < 0.05$).

TABLE 6

Localizing blue spots on twelve cultivars when inoculating with Agrobacterium strains (with GUS gene)

| Cultivar | No. Of explants | No. Of total explants having blue spots | % | No. Of explants having blue spots on regenerable end of hypocotyl | % |
|---|---|---|---|---|---|
| Vernal | 6 | 4 | 66.6 | 1 | 16.7 |
| Essex | 5 | 5 | 100 | 2 | 40.0 |
| Centennial | 10 | 3 | 30.0 | 1 | 10.0 |
| Lamar | 5 | 4 | 80.0 | 2 | 40.0 |
| Manokin | 8 | 3 | 37.5 | 1 | 12.5 |
| Hartwig | 7 | 6 | 85.7 | 3 | 42.9 |
| York | 10 | 4 | 40 | 3 | 30.0 |
| Lyon | 5 | 2 | 40 | 2 | 40.0 |
| Epps | 9 | 7 | 77.8 | 2 | 22.2 |
| Crawford | 12 | 5 | 41.7 | 2 | 16.7 |
| Sharkey | 10 | 5 | 50.0 | 3 | 30.0 |
| PI 398469 | 5 | 0 | 0 | 0 | 0 |

TABLE 7

GUS Expression for Soybean (cv. Lyon) hypocotyl Transformation Using Biolistic Method.

Transient GUS expression

| Total explants bombarded | % of explants having blue spots | Mean of blue spots per explant bombarded |
|---|---|---|
| 60 | 100 | 56.7 |

Stable GUS expression

| 3–4 weeks after selection on PPT medium | | | | 8 weeks after selection on PPT medium | | | |
|---|---|---|---|---|---|---|---|
| Total explants bombarded | % of explants on regenerated shoots, buds and mesitemoids | Mean of regenerated shoots, buds and mesitemoids having blue sectors per explant bombarded | Number of intact blue shoots and buds | Total explants bombarded | % of explants having intact blue shoots, buds and mesitemoids | Mean of intact blue shoots and buds per explant bombarded | Mean of intact blue meristemoid per explant bombarded |
| 31 | 83.4 | 4.7 | 3 | 11 | 100 | 3.6 | 4.5 |

REFERENCES

1. Amberger, L. A.; Palmer, R. G.; Shoemaker, R. C. Analysis of culture-induced variation in soybean. Crop Sci. 32:1103–1108; 1992.
2. Bailey, M. A.; Boerma, H. R.; Parrott, W. A. Genotype-specific optimization of plant regeneration from somatic embryos of soybean. Plant Sci. 93: 117–120; 1993.
3. Barwale, U. B.; Kerns, H. R.; Widholm, J. M. Plant regeneration from callus cultures of several soybean genotypes via embryogenesis and organogenesis. Planta 167: 473–481; 1986.
4. Barwale, U. B.; Meyer, M. M.; Widholm, J. M. Screening of *Glycene max.* and *Glycine soja* genotypes for multiple shoot formation at the cotyledonary node. Theor. Appl. Genet. 72: 423–428; 1986.
5. Barwale, U. B.; Widholm, J. M. Somaclonal variation in plants regenerated from cultures of soybean. Plant Cell Rpt. 6:365–368; 1987.
6. Buising, C. M.; Shoemaker, R. C.; Benbow, R. M. Early events of multiple bud formation and shoot development in soybean embryonic axes treated with the cytokinin, 6-benzylaminopurine. Amer. J. Bot. 81: 1435–1448; 1994.
7. Chang, H. H.; Chan, M. T. *Agrobacterium tumefaciens*-mediated transformation of soybean (*Glycine max* (L.) Merr.) is promoted by the inclusion of potato suspension culture. Bot. Bull. Acad. Sin. 32: 171–178; 1991.
8. Christou, P.; McCabe, D. E.; Swain, W. F., et al. Legume transformation. In: Verma, D. P. S., ed. Control of plant gene expression. Boca Raton, Fla.; CRC Press. Inc.; 1992:547–564.
9. Freytag, A. H.; Rao-Arelli, A. P.; Anand, S. C., et al. Somacional variation in soybean plants regenerated from tissue culture. Plant Cell Rpt. 8:199–202; 1989.
10. Gamborg, O. L.; Miller, R. A.; Ojima, R. A. Nutrient requirements of suspension culture of soybean root cells. Exp. Cell. Res. 50:151–158; 1968.
11. Graybosch, R. A.; Edge, M. E.; Delannay, X. Somacional variation in soybean plants regenerated from the cotyledonary node tissue culture system. Crop Sci. 27:803–806; 1987.
12. Hawbaker, M. S.; Fehr, W. R.; Mansur, L. M., et al. Genetic variation for quantitative traits in soybean lines derived from tissue culture. Theor. Appl. Genet. 87:49–53; 1993.
13. Hinchee, M. A.; Conner-Ward, D. V.; Newell, C. A., et al. Production of transgenic soybean plants using Agrobacterium-mediated DNA transfer. Bio/Technology 6:915–922; 1988.
14. Kameya, T.; Widholm, J. Plant regeneration from hypocotyl sections of Glycine species. Plant Sci. Lett. 21:289–294; 1981.
15. Kimball, S. L.; Bingham, E. T. Adventitious bud development of soybean hypocotyl sections in culture. Crop Sci. 13:758–760; 1973.
16. Mante, S.; Scorza, R.; Cordts, J. A simple, rapid protocol for adventitious shoot development from mature cotyledons of *Glycine max* cv Bragg. In Vitro Cell. Dev. Biol. 25P:385–388; 1989.
17. Murashige, T.; Skoog, F. A revised medium for rapid growth and bioassay with tobacco tissue cultures. Physiol. Plant. 15:473–497; 1962.
18. Pandey, P.; Bansal, Y. K. Plant regeneration from leaf and hypocotyl explants of *Glycine wightii* (W. and A.) Verdc. var *longicauda*. Japan. J. Breed. 42:1–5; 1992.
19. Parrott, W. A.; Williams, E. G.; Hildebrand, D. F., et al. Effect of genotype on somatic embryogenesis from immature cotyledons of soybean. Plant Cell Tissue Organ Cult. 16:15–21; 1989.
20. Poehlman, J. M.; Sleper, D. A. Breeding field crops, 4th Ed. Breeding soybeans. Ames, Iowa; Iowa State University; 1995:300–317.
21. Stephens, P. A.; Nickell, C. D.; Widholm, J. M. Agronomic evaluation of tissue-culture-derived soybean plants. Theor. Appl. Genet. 82:633–635; 1991.
22. Widholm, J. M.; Rick, S. Shoot regeneration from *Glycine canescens* tissue culture. Plant Cell Rpt. 2:19–20; 1983.
23. Wright, M. S.; Koehler, S. M.; Hinchee, M. A., et al. Plant regeneration by organogenesis in *Glycine max*. Plant Cell Rpt. 5:150–154; 1986.
24. Wright, M. S.; Ward, D. V.; Hinchee, M. A., et al. Regeneration of soybean (*Glycine max* L. Merr.) from primary leaf tissue. Plant Cell Rpt. 6:83–89; 1987.
25. Wright, M. S.; Williams, M. H.; Pierson, P. E., et al. Initiation and propagation of *Glycine max* L. Merr.: plants from tissue-cultured epicotyls. Plant Cell Tissue Organ Cult. 8:83–90; 1987.

List of References

Hoskin, R. L. Service, USDA Econom. Res., 1987: 1–35.
Smith, K. J.; Huyser, W. World distribution and significance of soybean. In J. R. Wilcox (ed.) Soybean: Improvement, production and uses. ASA, CSSA, SSSA, Madison, Wis. 1987:1–22.
Christou, P.; McCable, D. E.; Martinell, B. J.; Swain, W. F. Soybean genetic engineering-commercial production of transgenic plants. TIBTECH 8:145–151; 1990.
Liu, W.; Moore, P. J.; Collins, G. B. Somatic embrygenesis in soybean via somatic embryo cycling. In Vitro Cell. Dev. Biol. 28P:153–160; 1992.
Kartha, K. K.; Pahl, K.; Leuno, N. L.; Mroginski, L. A. Plant regeneration from meristems of grain legumes: soybean, cowpea, peanut, chickpea, and bean. Can. J. Bot. 59:1671–1679; 1981.
Yeh, M. S.; Chyuan, J. H. In vitro culture of immature soybean embryos III. Organogenesis studies on soybean embryogenic axes culture. J. Agric. Assoc. China 40:77–90; 1991.
Powell, W., Dunwell, J. M. In vitro genetics of barley (*Hordeum vulgare* L.): Response of immature embryos to 2,4-dichlorophenoxyacetic acid. Heredity 58: 75–80; 1987.
Komatsuda, T.; Kaneko, K.; Oka, S. Geneotype X sucrose interactions for somatic embrygenesis in soybean. Crop Sci. 31:333–337; 1991.
Christensen, A. H.; Quail, P. H. Ubiquitin promoter-based vectors for high-level expression of selectable and/or screenable marker genes in monocotyledonous plants. Transgenic Res. 5:213–218; 1996.

What is claimed is:

1. A method of regenerating soybeans (*G. max*) via organogenesis, comprising:
   obtaining hypocotyl explants from germinated seedlings of soybean plants whose regeneration is desired,
   maintaining said hypocotyl explants on a shoot induction medium comprising a cytokinin until shoots form at the acropetal end of said hypocotyl explant,
   excising shoots from said hypocotyl explant and maintaining said shoots on a shoot elongation medium until said shoots are competent on a rooting medium, and maintaining said shoots on a rooting medium until rooted plantlets are formed, and
   transplanting said plantlets to soil.

2. The process of claim 1, wherein said hypocotyl explant is split longitudinally, and said explant is placed, split-side down, on said shoot induction medium.

3. The method of claim 1, wherein said hypocotyl explant is maintained intact, and laid on its side or placed upright on said shoot induction medium such that the basipetal end of said explant is submerged in said medium.

4. The method of claim 1, wherein said explant is maintained under continuous darkness while on said shoot induction medium.

5. The method of claim 1, wherein said explant is maintained on a 16 hr photoperiod while on said shoot initiation/elongation medium.

6. The method of claim 1, wherein said shoot induction medium comprises benzyladenine.

7. A method for transforming soybean plants to express exogenous DNA, comprising:

obtaining a hypocotyl explant from germinated seedlings of a soybean plant, maintaining said explant on a shoot induction medium comprising a cytokinin for 16–32 hours, bombarding said explant, with the acropetal end facing up, with microparticles of an inert metal coated with exogenous DNA comprising a plasmid which comprises an expression gene, said expression gene encoding the expression of a protein exogenous to said soybean plant, maintaining said bombarded hypocotyl explant on a medium selective for growth of transformed tissues, followed by maintenance on a shoot elongation medium and preparing plantlets from shoots so obtained.

8. The process of claim 7, wherein said plantlets are obtained by regeneration according to the process of claim 1.

9. The process of claim 7, wherein said plasmid comprises a gene whose expression product may be detected by a flourometric or histochemical assay or procedure for detecting foreign DNA, and said bombarded hypocotyl plants, following growth on a medium selected for transformed tissues, are assayed for expression of said gene by said assay or procedure.

10. A method of transforming soybeans, comprising obtaining a hypocotyl soybean explant from germinated seedlings, and maintaining on its side or upright on a shoot induction medium comprising a cytokinin with a basipetal end thereof submerged in said medium, pre-culturing and/or co-culturing an Agrobacterium strain with a virulence enhancing substance, and adding said pre- or co-cultured bacteria to the acropetal end of said upright hypocotyl explant or by complete submersion, co-incubating said hypocotyl explant for a time sufficient to permit transfection of said hypocotyl explant by said bacteria, disinfecting said hypocotyl explant, maintaining said hypocotyl explant on a shoot induction medium and assaying said explant for expression of introduced foreign DNA, and regenerating hypocotyl explants positive for expression of said DNA.

11. The process of the claim 10, wherein said regeneration is effected pursuant to the process of claim 1.

* * * * *